US011126819B1

(12) United States Patent
Alqattan

(10) Patent No.: US 11,126,819 B1
(45) Date of Patent: Sep. 21, 2021

(54) SYSTEMS AND METHODS FOR OPTIMIZING CAMERA AND MICROSCOPE CONFIGURATIONS FOR CAPTURING THIN SECTION IMAGES

(71) Applicant: Saudi Arabian Oil Company, Dhahran (SA)

(72) Inventor: Hussain Alqattan, Hofuf (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/924,527

(22) Filed: Jul. 9, 2020

(51) Int. Cl.
*G06K 9/00* (2006.01)
*G06T 7/66* (2017.01)

(52) U.S. Cl.
CPC ............ *G06K 9/00127* (2013.01); *G06T 7/66* (2017.01); *G06T 2207/10056* (2013.01)

(58) Field of Classification Search
None
See application file for complete search history.

(56) References Cited

U.S. PATENT DOCUMENTS

| | | | | |
|---|---|---|---|---|
| 4,868,883 A * | 9/1989 | Chen | .................. | G06K 9/00127 382/109 |
| 6,495,106 B1 | 12/2002 | Kalra et al. | | |
| 8,000,511 B2 | 8/2011 | Perz | | |
| 8,311,788 B2 * | 11/2012 | Hurley | .................... | G06T 17/00 703/9 |
| 8,676,556 B2 * | 3/2014 | Deffenbaugh | ....... | G01N 23/046 703/10 |
| 9,626,771 B2 | 4/2017 | Mezghani et al. | | |
| 9,996,924 B2 | 6/2018 | Chukka et al. | | |
| 10,900,351 B2 * | 1/2021 | Deffenbaugh | .......... | E21B 47/09 |
| 11,010,883 B2 * | 5/2021 | Anifowose | .......... | G06K 9/4652 |
| 2009/0238435 A1 | 9/2009 | Shields | | |
| 2010/0198638 A1 * | 8/2010 | Deffenbaugh | ....... | G01N 23/046 705/308 |
| 2011/0004448 A1 * | 1/2011 | Hurley | .................... | G06T 17/00 703/1 |

(Continued)

OTHER PUBLICATIONS

Budennyy, Semen et al.; "Image Processing and Machine Learning Approaches for Petrographic Thin Section Analysis" SPE-187855-MS, SPE Russian Petroleum Technology Conference, Oct. 16-18, 2017; pp. 1-12.

(Continued)

*Primary Examiner* — Anand P Bhatnagar
(74) *Attorney, Agent, or Firm* — Bracewell LLP; Constance G. Rhebergen; Vivek P. Shankam

(57) ABSTRACT

Systems and methods for method for optimizing settings of a camera and microscope for capturing thin section images of a reservoir rock in a hydrocarbon reservoir. The method includes performing a frequency analysis of each pixel of the thin section image, associating each pixel in the thin section image with a class identifier selected from a plurality of class identifiers, each class identifier associated with range of frequencies, determining a percentage of pixels in each class identifier, determining a percentage of pixels comprising noise, generating a machine learning model using a structured data set, and determining, using the machine learning model, an optimized setting for the camera and an optimized setting for the microscope based on the thin section image with the least noise.

20 Claims, 8 Drawing Sheets

(56) References Cited

U.S. PATENT DOCUMENTS

| | | |
|---|---|---|
| 2012/0127297 A1 | 5/2012 | Baxi et al. |
| 2017/0285319 A1 | 10/2017 | Xu et al. |
| 2019/0318467 A1* | 10/2019 | Anifowose .......... G02B 21/365 |
| 2019/0339203 A1* | 11/2019 | Miller ................ G01N 21/6486 |
| 2021/0010936 A1* | 1/2021 | Hegazi .................. G01N 21/94 |
| 2021/0090239 A1* | 3/2021 | Pattnaik ................ G06N 3/088 |

OTHER PUBLICATIONS

Fueten, Frank; "A Computer-Controlled Rotating Polarizer Stage for the Petrographic Microscope" PII: S0098-3004 (96)00079-9, Computers & Geosciences vol. 23, No. 2, 1997; pp. 203-208.

* cited by examiner

SYSTEMS AND METHODS FOR OPTIMIZING CAMERA AND MICROSCOPE CONFIGURATIONS FOR CAPTURING THIN SECTION IMAGES

BACKGROUND

Field of the Disclosure

The present disclosure generally relates to methods for analyzing petrographic thin section images.

Description of the Related Art

Core samples are collected from wells during drilling so that they can be analyzed to determine certain characteristics of rock formations for particular well sections. The core samples are often collected during drilling from what is anticipated to be the productive reservoir sections of a well. Petrographic thin section samples can then be prepared from plug that is extracted from sections of the core samples. After the petrographic thin section samples are prepared, images are produced from the petrographic thin section samples by using a high-resolution polarizing microscope that photographs the petrographic thin section samples.

A common issue in geological petrography work is the analysis of thin sections. Thin section analysis may be used to determine properties of the thin section such as mineral composition and texture. Hydrocarbon fluids may be found in the pore spaces visible in thin sections. The study of geological thin sections has become one of the most important disciplines for hydrocarbon exploration. Conventionally, thin section analysis has been performed by a point counting method. Point counting in thin sections is normally conducted through mechanical or electromechanical devices attached to a microscope. Such mechanical and electromechanical devices can be expensive and offer limited functionality. The final results of point counting analysis are subjective and dependent on expertise of the user who performed the point counting.

SUMMARY

This specification describes a system implemented as computer programs on one or more computers in one or more locations that performs automated analysis of petrographic thin section images.

One embodiment is a method for optimizing settings for a camera and microscope for capturing thin section images of a reservoir rock in a hydrocarbon reservoir. The method may include extracting a plurality of core samples from a well, cutting a respective plurality of thin sections from the plurality of core samples, and capturing a thin section image using a robotic microscope and a camera. The method may further include performing a frequency analysis of each pixel of the thin section image, associating each pixel in the thin section image with a class identifier selected from a plurality of class identifiers, each class identifier associated with range of frequencies, determining a percentage of pixels in each class identifier, and determining a percentage of pixels comprising noise. The method may further include saving the thin section image and the settings for the camera and microscope associated with the thin section image, saving data generated from the frequency analysis of the thin section image, and saving the determination of the percentage of pixels comprising noise associated with the thin section image. The method may further include repeating these steps for a plurality of thin section images taken at a plurality of settings for the camera and the microscope. The method may also include combining the settings for the camera and microscope associated with the plurality of thin section images, data generated from the frequency analysis of the plurality of thin section images, and the determination of the percentage of pixels comprising noise associated with the plurality of thin section images to produce a structured data set, generating a machine learning model using the structured data set, and determining, using the machine learning model, an optimized setting for the camera and an optimized setting for the microscope based on the thin section image with the least noise.

In one embodiment, the step of determining a percentage of pixels comprising noise further comprises determining a percentage of pixels having a frequency over a predetermined threshold. The machine learning model comprises an artificial neural network (ANN), a support vector machine (SVM), a radial basis function (RBF), fuzzy logic, a decision tree, random forest, or k-means algorithm. The plurality of settings comprise magnification, illumination, stage position, plane polarized light (PPL), cross polarized light (XPL), thin focus, or coarse focus. The optimized setting comprises at least one setting for magnification, illumination, stage position, plane polarized light (PPL), cross polarized light (XPL), thin focus, and coarse focus.

Another example embodiment is a system including a microscope configured to take images of a plurality of petrographic thin section samples and create petrographic thin section sample digital image files from the images, and a computer system comprising a processor and a non-transitory computer readable storage medium in data communication with the processor storing instructions executable by the processor and that upon such execution causes the processor to perform some operations. The operations may include performing a frequency analysis of each pixel of the thin section image, associating each pixel in the thin section image with a class identifier selected from a plurality of class identifiers, each class identifier associated with range of frequencies, determining a percentage of pixels in each class identifier, and determining a percentage of pixels comprising noise. The operations may further include saving the thin section image and the settings for the camera and microscope associated with the thin section image, saving data generated from the frequency analysis of the thin section image, and saving the determination of the percentage of pixels comprising noise associated with the thin section image. The operations may further include repeating these steps for a plurality of thin section images taken at a plurality of settings for the camera and the microscope. The operations may also include combining the settings for the camera and microscope associated with the plurality of thin section images, data generated from the frequency analysis of the plurality of thin section images, and the determination of the percentage of pixels comprising noise associated with the plurality of thin section images to produce a structured data set, generating a machine learning model using the structured data set, and determining, using the machine learning model, an optimized setting for the camera and an optimized setting for the microscope based on the thin section image with the least noise.

Another example embodiment is a non-transitory computer readable storage medium storing instructions executable by a data processing apparatus and that upon such execution causes the data processing apparatus to perform some operations. The operations may include performing a frequency analysis of each pixel of the thin section image, associating each pixel in the thin section image with a class identifier selected from a plurality of class identifiers, each class identifier associated with range of frequencies, determining a percentage of pixels in each class identifier, and determining a percentage of pixels comprising noise. The operations may further include saving the thin section image and the settings for the camera and microscope associated with the thin section image, saving data generated from the frequency analysis of the thin section image, and saving the determination of the percentage of pixels comprising noise associated with the thin section image. The operations may further include repeating these steps for a plurality of thin section images taken at a plurality of settings for the camera and the microscope. The operations may also include combining the settings for the camera and microscope associated with the plurality of thin section images, data generated from the frequency analysis of the plurality of thin section images, and the determination of the percentage of pixels comprising noise associated with the plurality of thin section images to produce a structured data set, generating a machine learning model using the structured data set, and determining, using the machine learning model, an optimized setting for the camera and an optimized setting for the microscope based on the thin section image with the least noise.

The thin section analysis system as described in this specification uses advanced machine learning and automated image processing methods to process thin section images and achieves several advantages over manual systems for thin section image analysis. First, the thin section analysis system as described in this specification can be implemented to perform thin section image analysis orders of magnitude faster than manual methods for thin section image analysis (such as point counting methods). For example, the thin section analysis system as described in this specification can be implemented to process thin section images in two minutes or less, whereas conventional point counting methods (that require a geologist to manually examine the thin section images at a large number of different points) may take up to four hours. Second, the thin section analysis system as described in this specification may be more accurate than manual methods for thin section image analysis. For example, the thin section analysis system as described in this specification relies on machine learning and automated image analysis algorithms and thereby obviates sources of human error that are present in manual methods for thin section image analysis. For example, point counting methods for thin section image analysis place a high cognitive burden on the user performing the point counting method, increasing the likelihood of human errors such as the user incorrectly counting the number of grains or pores in a region of a thin section image. Third, the thin section analysis system as described in this specification is consistent and eliminates potential biases present in manual methods for thin section image analysis. For example, a user that performs a point counting method multiple times on a single thin section image to determine an estimate of a characteristic of a thin section image (for example, the average diameter of grains in the thin section) may determine different values each time. In contrast, the thin section analysis system as described in this specification will determine consistent estimates of the same characteristic.

The thin section analysis system as described in this specification performs a comprehensive analysis of the thin section characteristics, including both the compositional properties of the thin section (for example, the fraction of the thin section occupied by pores) and properties of the grains of the thin section (for example, the distribution of grain diameters in the thin section). In contrast, many conventional thin section analysis systems perform a less comprehensive analysis by identifying fewer relevant properties of thin sections. The thin section analysis system as described in this specification is fully automated and thereby enables more efficient use of computational resources than conventional systems that are not fully automated. Conventional systems that are not fully automated require user intervention (for example, to manually calibrate system parameters). User intervention can be time consuming (potentially ranging from seconds to hours), and during user intervention the computational resources of such conventional systems (for example, processing power) are not utilized. Since the thin section analysis system as described in this specification is fully automated it can operate continuously and thereby utilize computational resources more efficiently.

BRIEF DESCRIPTION OF THE DRAWINGS

The foregoing aspects, features, and advantages of embodiments of the present disclosure will further be appreciated when considered with reference to the following description of embodiments and accompanying drawings. In describing embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

DETAILED DESCRIPTION

Figure 1:
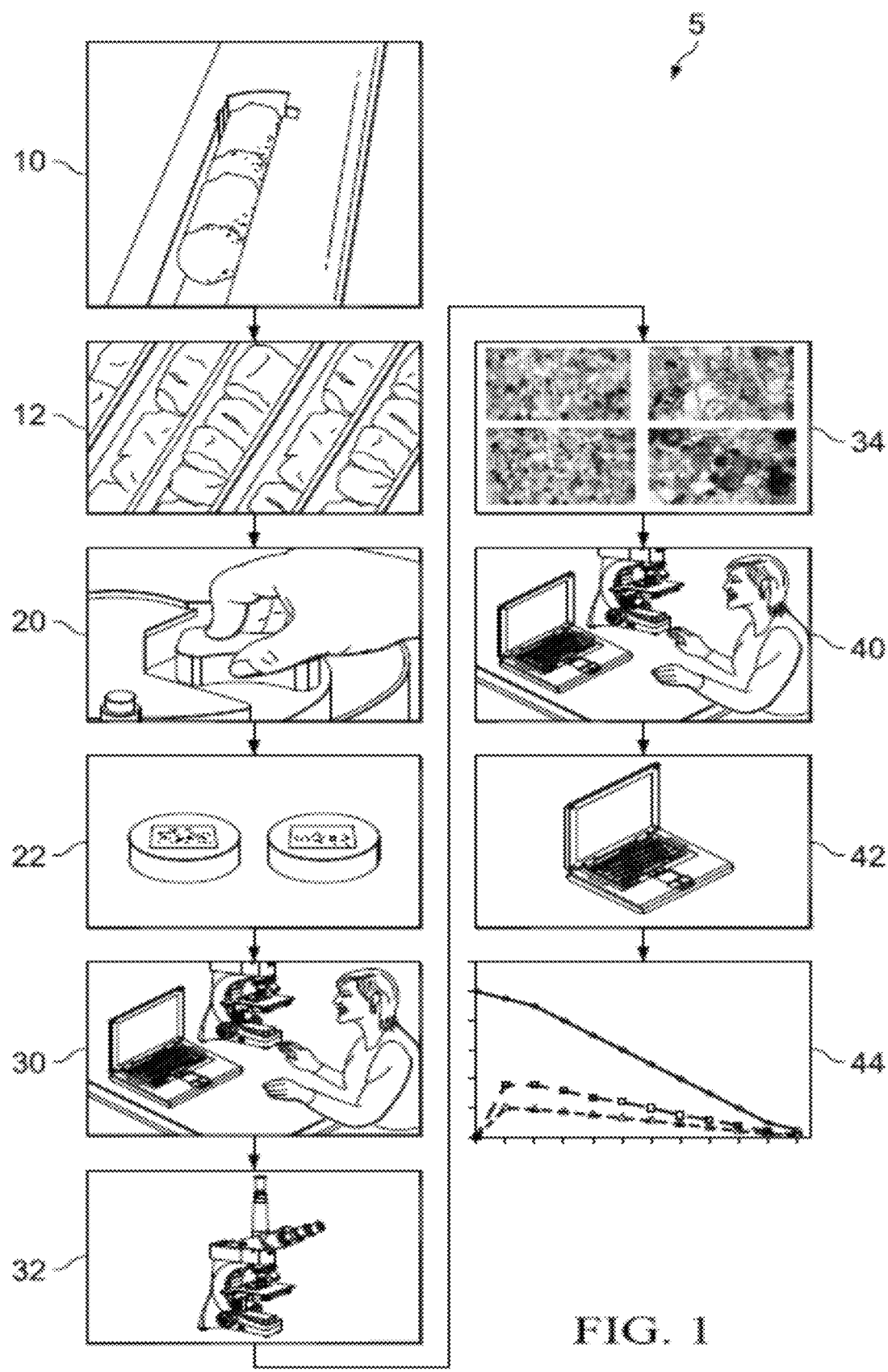
FIG. 1 illustrates a flow chart of an example core extraction through petrographic thin section sample analysis system and method in accordance with an embodiment of the disclosure.

The present disclosure will be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

For simplicity and clarity of illustration, the drawing figures illustrate the general manner of construction, and descriptions and details of well-known features and techniques may be omitted to avoid unnecessarily obscuring the discussion of the described embodiments. Additionally, elements in the drawing figures are not necessarily drawn to scale. For example, the dimensions of some of the elements in the figures may be exaggerated relative to other elements to help improve understanding of the various example embodiments.

According to an embodiment, and as illustrated in reference to FIG. 1, an example core extraction through petrographic thin section sample analysis system and method system 5 is shown. FIG. 1 illustrates an example layout of a particular system 5 starting with the extraction of core samples or "core plugs" from a well 10. Following the step of extracting a core sample from a well 10, multiple samples are organized by the depth they were collected 12, and transported to a laboratory for further analysis. Once at the laboratory the next step is cutting core samples further into smaller plugs 20 that can be sliced into petrographic thin section samples 22. After the petrographic thin section samples 22 are prepared, the next step is to scan the thin section samples in the laboratory 30 with a high-resolution polarizing microscope 32. The microscope can be a robotic microscope including a control system for controlling the magnification, illumination, stage position, plane polarized light (PPL), cross polarized light (XPL), thin focus, or coarse focus of the microscope. In the next step, images 34 that are representative of each petrographic thin section sample are output from the high-resolution polarizing microscope 32. A technician then loads the images into a processing program 40 on a computer system 42. The computer system 42 utilizes specialized software that generates permeability estimations for each of the images 34 that are representative of each petrographic thin section sample 22. Throughout the process the original collection depth of the core and subsequent petrographic thin section samples are tracked such that the depth information can be input into the computer system 42 and logged along with the permeability estimations for each petrographic thin section sample 22. The characteristics of the subsurface formation over various depths can then be graphed or turned into another visualized output 44 that is helpful for making decisions about the plan for a particular well. In an embodiment the permeability and depth information for each of the petrographic thin section samples can be stored into a database for additional analysis and processing. Other information about the samples or permeability estimates can also be stored in the database. For example, the well location, time of collection, time of analysis, or other information may also be stored in the database and associated with a particular petrographic thin section sample.

Figure 2:
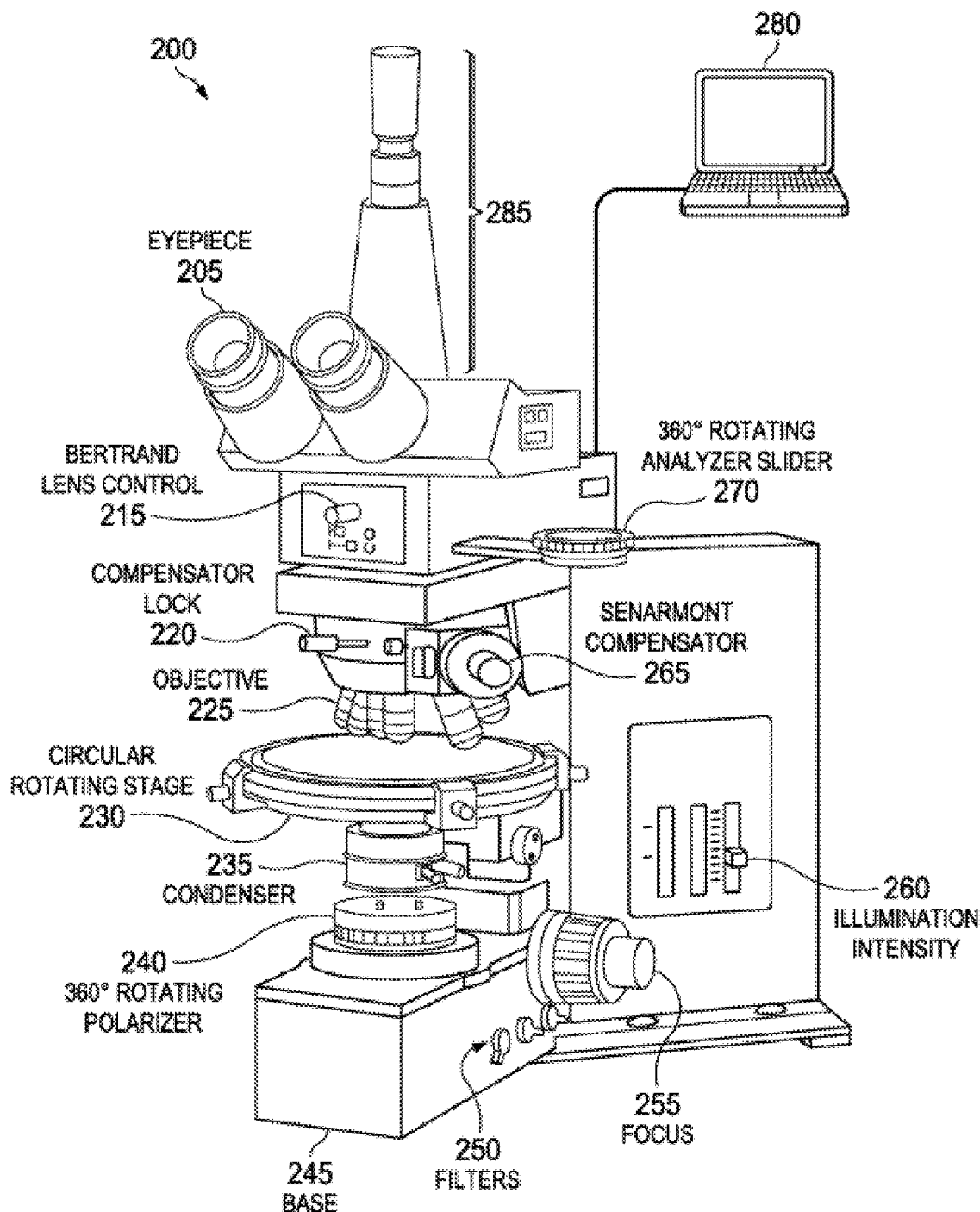
FIG. 2 illustrates an implementation of a polarizing robotic microscope used for an image-based analysis of a geological thin section in accordance with an embodiment of the disclosure.

Turning briefly to FIG. 2, an implementation of a robotic polarizing microscope system 200 that may be used for an image-based analysis of the geological thin section 22 is illustrated. Geological thin sections, such as geological thin section 22, can be examined using the polarizing microscope system 200 to examine the grains and pores of the geological thin section 22. The microscope system 200 uses polarized light, because the light waves vibrate in one direction, whereas in normal light, the light waves vibrate in random directions.

The primary components of the polarizing microscope system 200 include: a rotating stage 230, polars 240, a Bertrand lens control 215, a Senarmont compensator 265, a rotating analyzer slider 270, an objective 225 beam-splitter prism, a high-resolution digital camera system with extension tube 285, and a condenser 235 beam-splitter prism. The rotating stage 230 supports the geological thin section 22 during observation. In this implementation, the rotating stage 230 is a 360-degree circular rotating stage to facilitate view of the geological thin section 22 at different rotational perspectives. The polars 240 include polarizing and analyzing devices or filter and may be placed above and below the rotating stage 230. In this implementation, the polars 240 allow light to pass through in a north-south (N-S) vibration direction and is placed below the rotating stage 230. The Bertrand lens control 215 allows observation in a conoscopic view where it brings the image of an interference figure into the focal plane of the ocular. The compensator 265 is held in place with a compensator lock 220 and helps determine the order of interference colors between crossed-nicols. The analyzer slider 270 allows light to pass through in an east-west (E-W) vibration direction. It is placed above the rotating stage 230.

Other optical accessories, such as a mica plate, a gypsum plate, and a quartz wedge, and, as are known, may be included in the polarizing microscope system 200. For example, the mica plate gives an interference color of first order white (as understood in optical microscopy). The gypsum plate gives a distinct magenta color at the boundary between first and second order colors. The quartz wedge helps produce interference colors and produce a range of retardations.

The polarizing microscope system 200 shown in FIG. 2 also includes standard components, such as the eyepiece 205, observation tubes 210, and a base 245 that supports the other components. Also included are a number of filters 250 and focus 255 as are known. There is also an illumination intensity control 260.

The polarizing microscope system 200 includes or is communicably coupled to a computing system 280. The computing system 280, in this implementation, is a microprocessor based computing system that includes one or more memory modules, one or more processors, input and output peripherals (including the polarizing microscope as an input), and other associated components. The computing system 280 may also include software in the form of instructions stored on the one or more memory modules and executable by the one or more processors to perform operations, either automatically without human intervention or with human input.

The polarizing microscope system 200 may facilitate viewing and image-capture of the geological thin section 22 in plane-polarized light and cross-polarized light. In plane-polarized light, many minerals are colorless, which makes it impossible to distinguish grain boundaries between two adjacent colorless grains. Similarly, in crossed-polarized light the interference color displayed depends on the mineral type, the orientation of the indicatrix of the grain with respect to the polarizers and the thickness of the thin section 22. Hence, two adjacent grains may have similar interference colors at some orientations of the thin section 22 with respect to the polarizers 240. If sufficient contrast between adjacent grains exists, the boundaries between them can be recognized.

If two adjacent grains in the geological thin section 22 show similar interference colors, the boundaries may be difficult to recognize. As explained more fully infra, the contrast between adjacent grains can be increased by rotating the thin section 22 relative to the polarizer 240 and analyzer 270. Thus, full visual recognition of grain boundaries of the grains of the rock sample in geological thin section 22 can be facilitated by using multiple thin section images taken at different angles of rotation. In this embodiment, the computer unit for performing the automated thin section analysis is connected to the camera, and the robotic control unit controls the settings for the microscope tools (magnification, illumination, stage position, plane polarized light (PPL) versus cross polarized light (XPL), and thin or coarse focus) in accordance with an embodiment of the disclosure.

Figure 3:
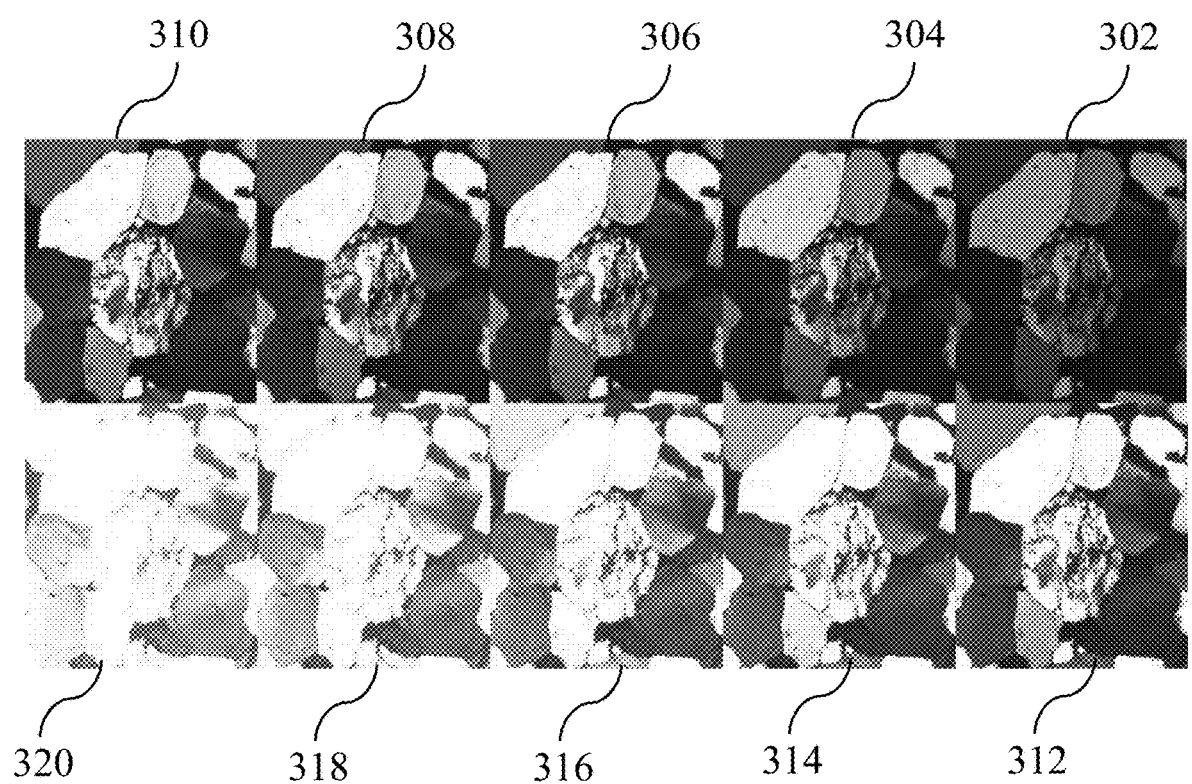
FIG. 3 illustrates an image-based analysis of a geological thin section in accordance with an embodiment of the disclosure.

FIG. 3 illustrates an image-based analysis of a geological thin section in accordance with an embodiment of the disclosure. An analysis of a single image of a thin section with increasing brightness from top right 302 to bottom left 320 with varying brightness from 5% to 95% in increments of 10%, including image 302 at 5% brightness, image 304 at 15% brightness, image 306 at 25% brightness, image 308 at 35% brightness, image 310 at 45% brightness, image 312 at 55% brightness, image 314 at 65% brightness, image 316 at 75% brightness, image 318 at 85% brightness, and image 320 at 95% brightness, shows that there is delineation of the edges between the grain and the overgrowth in the grain in the top left corner image 310 with low brightness. Additionally, the image on the right bottom corner 312 with high brightness does not appear to show delineation of the edges between the grain and the overgrowth in the grain. The edges of both grains have been distinguished at opposite sides of brightness spectrum in accordance with an embodiment of the present disclosure. FIG. 3 shows how changing the setting of brightness improves the edge continuity of some grains differently. If these images are shortened to one, then not all the edges on all of the grains can been discovered.

Figure 4:
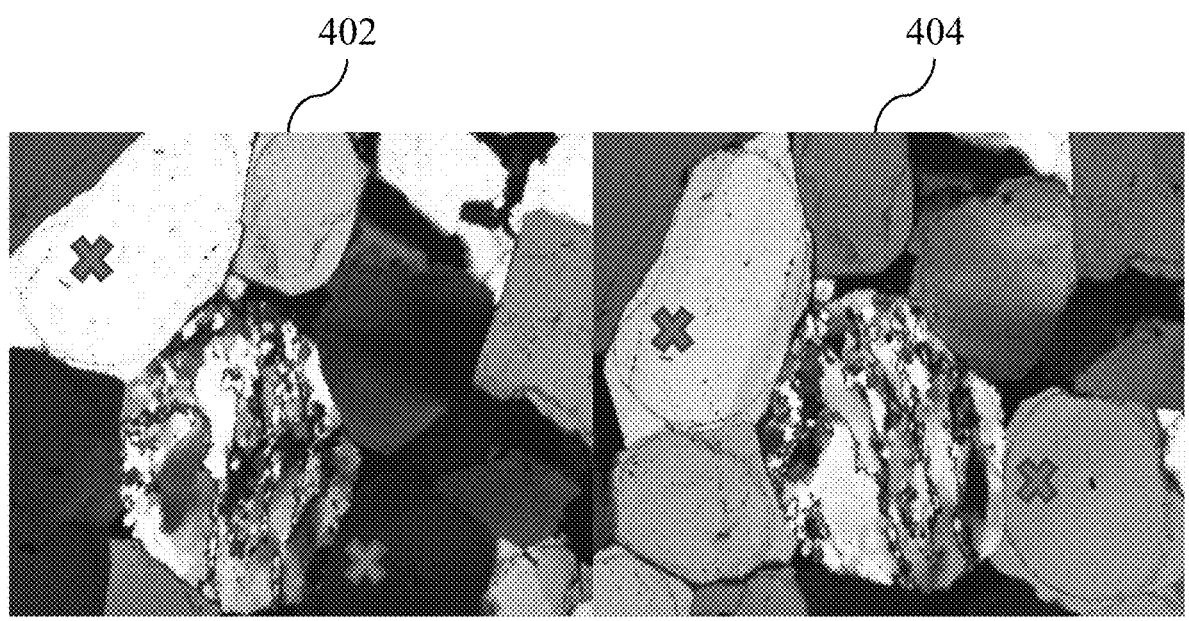
FIG. 4 illustrates an image-based analysis of a geological thin section in accordance with an embodiment of the disclosure.

FIG. 4 illustrates an image-based analysis of a geological thin section in accordance with an embodiment of the disclosure. In FIG. 4, both images 402, 404 have the same brightness of 33%, which is conventional for representative images for analysis. However, the one on the right 404 has 0 degrees orientation, while the one on the left 402 has 22.5 degree orientation. It can be noticed here that the change in orientation results in the detection of cleavage angle and detecting edges in grains marked with an X, in accordance with an embodiment of the disclosure. FIG. 4 shows how changing the orientation, usually used to detect cleavage angle, helps in detecting edges in grains. This means that the mere process of choosing representative images with pre-defined settings configuration would not guarantee optimal results since (1) not all possibilities have been analyzed, and (2) the automated programs responsible for analysis have not been involved in choosing the images that produce the optimal analysis. This specification discloses an automated optimization workflow for the best microscope and camera settings configuration by utilizing the automated analysis while the images are being captured and not after capturing the images.

Figure 5:
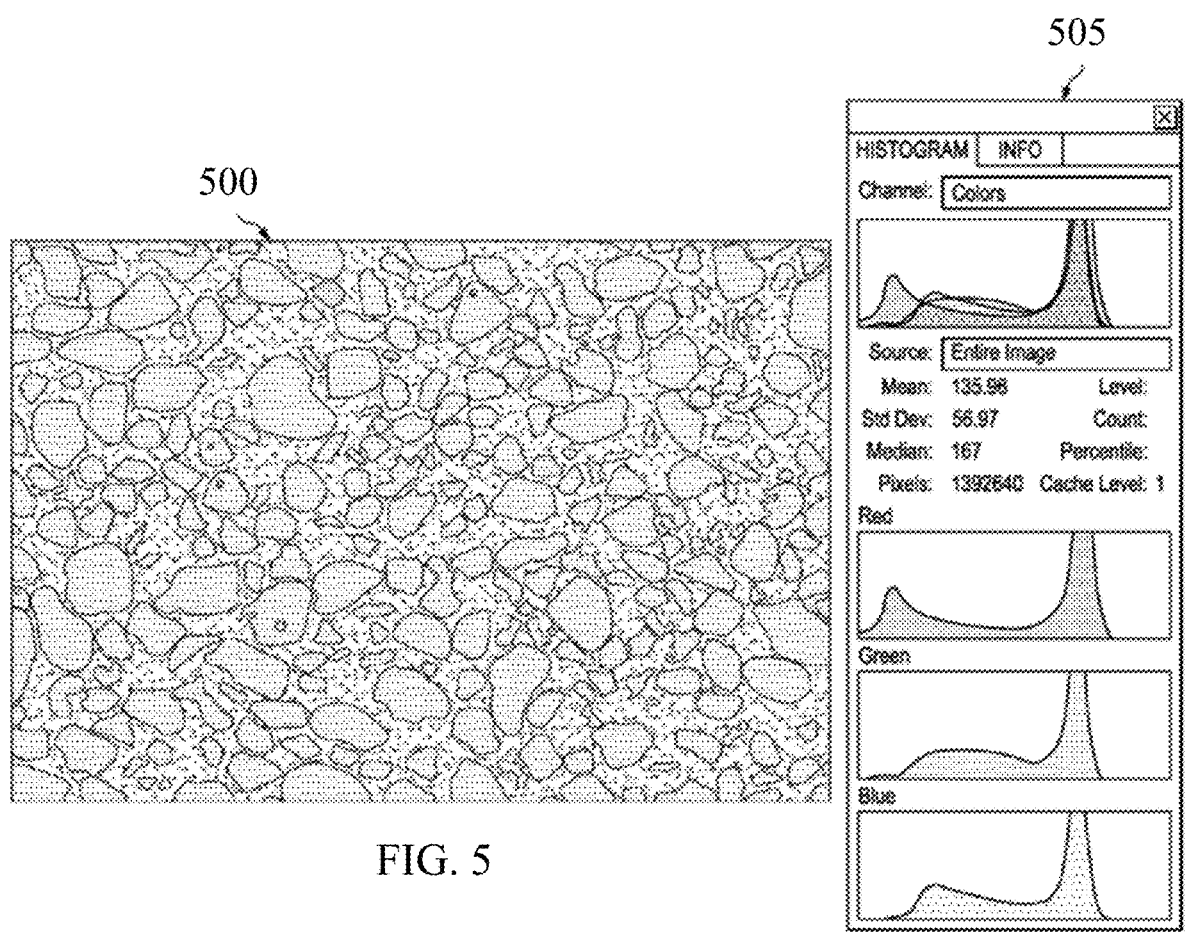
FIG. 5 illustrates another plane polarized image of the geological thin section in accordance with an embodiment of the disclosure.

FIG. 5 illustrates another plane polarized image of the geological thin section in accordance with an embodiment of the disclosure. Exclusion of the pore space may best be accomplished by using the plane-polarized image, since a histogram 505 of the plane-polarized image is bimodal as shown in FIG. 5. Indeed, as shown, image 500 shows that a clear cut-off can be determined or calculated to segment this image into a grain color and a pore color. This value can be applied to the plane-polarized image 500 to distinguish grains from pores more easily. In some aspects, the cut-off value may depend on a color of the dye epoxy used to prepare the geological thin section. For example, the cut-off value can be estimated manually for a particular geological thin section to be analyzed and then used for other geological thin sections to be analyzed, provided that the same epoxy is being used for all of the geological thin sections.

Figure 6:
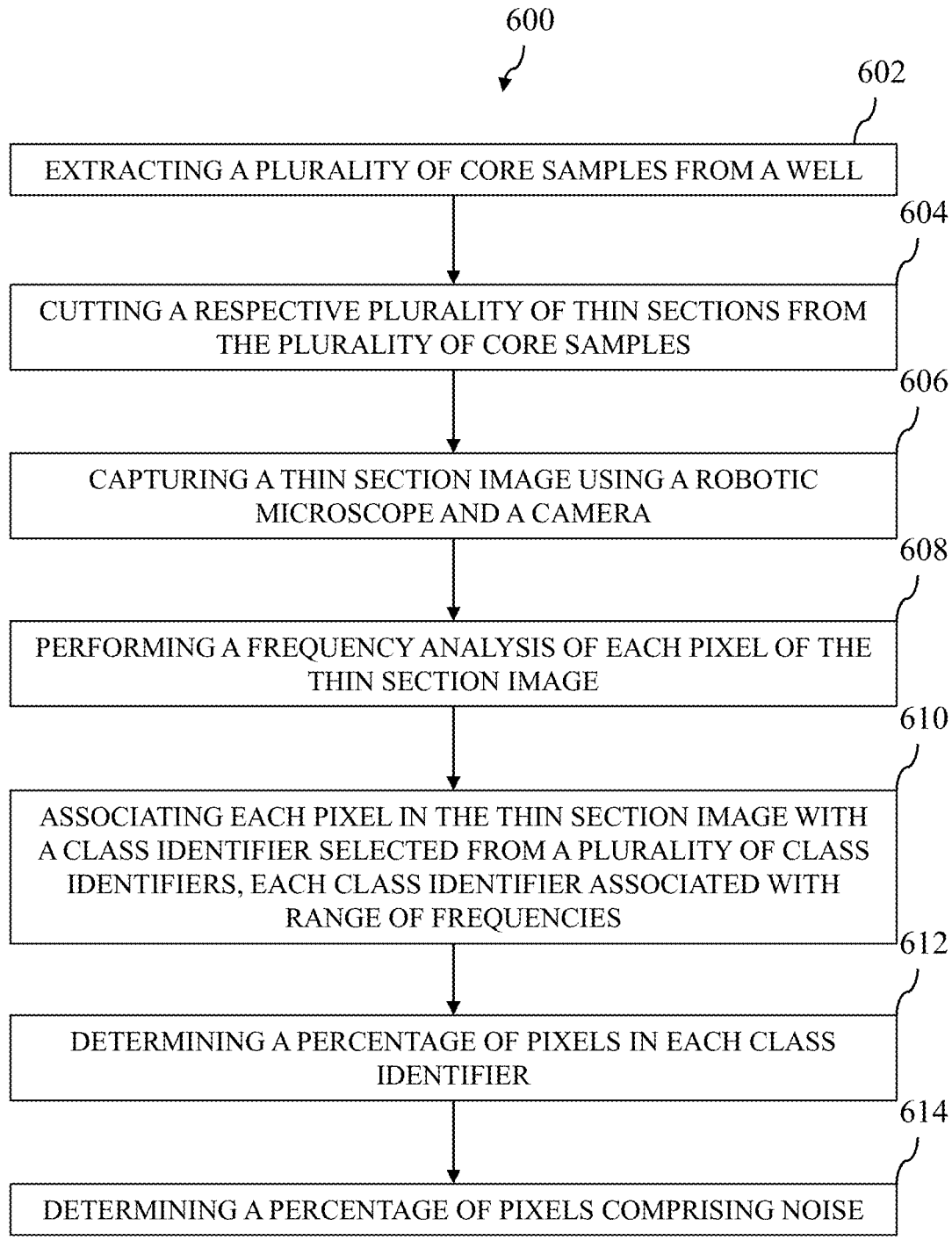
FIG. 6 illustrates example steps in a method for capturing an image by a robotic thin section analyzer in accordance with an embodiment of the disclosure.

FIG. 6 illustrates example steps in a method 600 for capturing an image by a robotic thin section analyzer in accordance with an embodiment of the disclosure. The method may be used for optimizing settings for a camera and microscope for capturing thin section images of a reservoir rock in a hydrocarbon reservoir. At step 602, the method includes extracting a plurality of core samples from a well. At step 604, the method involves cutting a respective plurality of thin sections from the plurality of core samples. At step 606, the method includes capturing a thin section image using a robotic microscope and a camera. At step 608, the method includes performing a frequency analysis of each pixel of the thin section image, and associating each pixel in the thin section image with a class identifier selected from a plurality of class identifiers, at step 610. Each class identifier may be associated with range of frequencies. At step 612, the method includes determining a percentage of pixels in each class identifier, and step 614 the method includes determining a percentage of pixels comprising noise. Method 600 may include additional steps, which are described with reference to FIG. 7 below.

Figure 7:
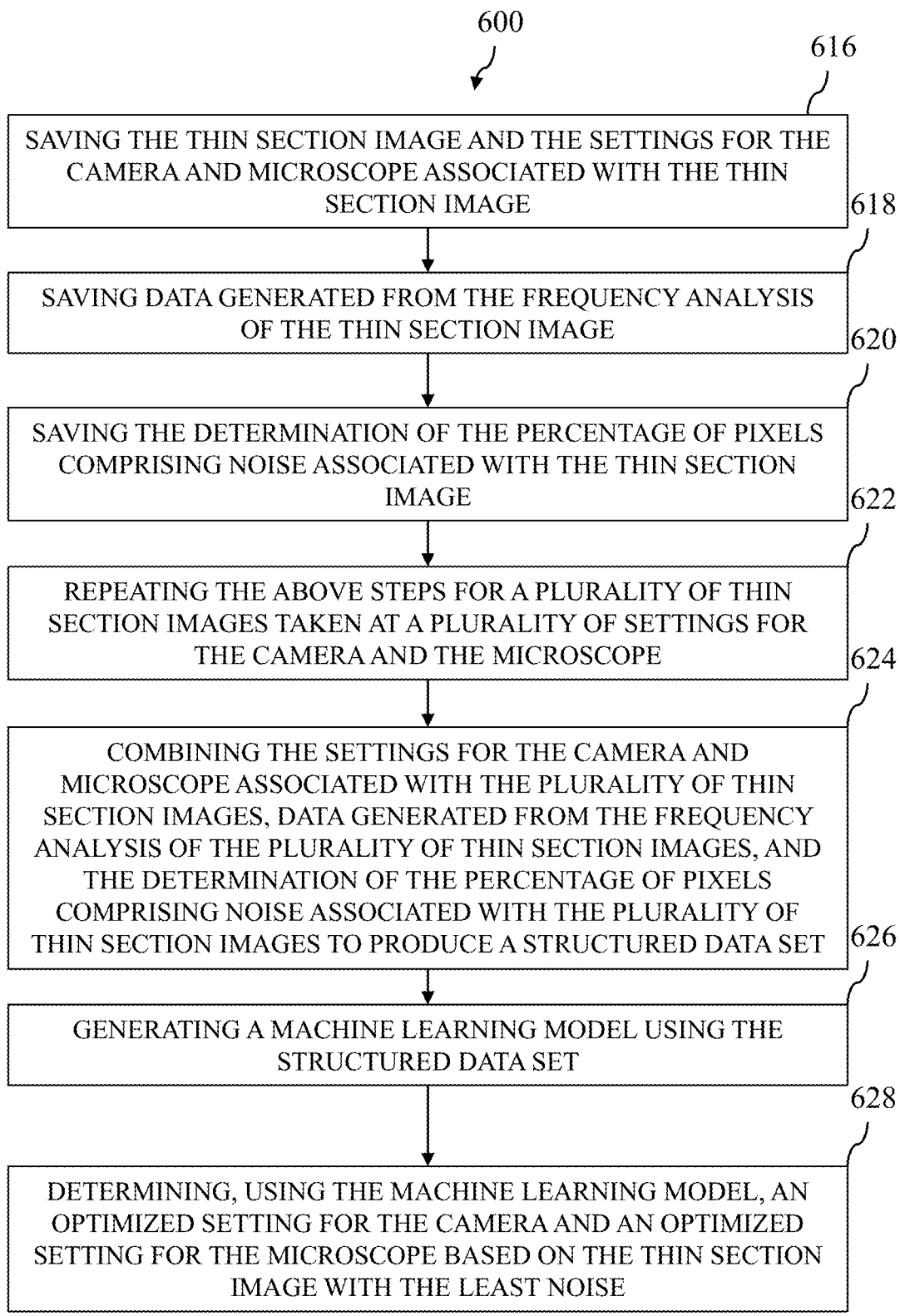
FIG. 7 illustrates example steps in a method for optimizing settings for a camera and microscope in accordance with an embodiment of the disclosure.

FIG. 7 illustrates additional steps in the method 600 for optimizing settings for a camera and microscope in accordance with an embodiment of the disclosure. As illustrated in step 616, the method may further include saving the thin section image and the settings for the camera and microscope associated with the thin section image. At step 618, the method may include saving data generated from the frequency analysis of the thin section image. At step 620, the method may include saving the determination of the percentage of pixels comprising noise associated with the thin section image. At step 622, the method may include repeating these steps for a plurality of thin section images taken at a plurality of settings for the camera and the microscope. At step 624, the method may include combining the settings for the camera and microscope associated with the plurality of thin section images, data generated from the frequency analysis of the plurality of thin section images, and the determination of the percentage of pixels comprising noise associated with the plurality of thin section images to produce a structured data set. At step 626, the method may include generating a machine learning model using the structured data set. At step 628, the method may include determining, using the machine learning model, an optimized setting for the camera and an optimized setting for the microscope based on the thin section image with the least noise.

In one embodiment, the step of determining a percentage of pixels comprising noise further comprises determining a percentage of pixels having a frequency over a predetermined threshold. The plurality of settings comprise magnification, illumination, stage position, plane polarized light (PPL), cross polarized light (XPL), thin focus, or coarse focus. The optimized setting comprises at least one setting for magnification, illumination, stage position, plane polarized light (PPL), cross polarized light (XPL), thin focus, and coarse focus.

FIGS. 6 and 7 depict a process 600 illustrating construction and operation of the machine learning model in accordance with an embodiment of the disclosure. In some embodiments, the machine learning engine may be use an artificial neural network (ANN), a support vector machine (SVM), a radial basis function (RBF), fuzzy logic, a decision tree, random forest, or k-means algorithm. A machine learning model may be trained by adjusting and optimizing learning parameters of the machine learning engine. Example learning parameters may include learning rate, number of neurons, number of layers, activation function, and weight coefficients.

The prior art methodologies for thin section image analysis compute red, green, and blue (RGB) values for every pixel and utilize different image processing toolboxes, pattern recognition techniques, and algorithms to detect different geological information. The information includes porosity, grain size, roundness, petrological properties, and other pre-defined objects and features such as fossils, and special grains (peloids, ooids). These are not all identifiable under the same settings configuration like magnification, plane polarized light (PPL) versus cross polarized light (XPL), orientation, focus of the microscope, and brightness of the camera, and some of them can only be identified by changing these parameters (or extinction angle). Conventionally, a geoscientist would have to change the settings configuration and perform an analysis in the lab. However, with the rise of automated microscope, thin section image acquisition, and automated analysis programs, and to reduce the processing time and storage size of images, only representative images are chosen to run the thin section analysis (for example, images with four or five different orientations, images with two different brightness). This led to potentially missing or even erroneous analysis results because the image processing capabilities of such automated programs is bound by the quality and consistency of thin section images. There could be potentially missing information from images that are not chosen or not taken under the right settings configuration that could have been analyzed.

One embodiment is an automated configuration system of image capturing settings (magnification, focus, brightness, orientation, plane polarized light (PPL) versus cross polarized light (XPL)) in microscope and camera. The best configuration is determined by automated object detection programs that can detect geological features and objects. The system quantifies the processing uncertainty of the object detection by comparing the variable results of different image settings. Additionally, the system aims to gives a measure of the thickness consistency of samples in thin sections as a quality check of their conditions.

Generally, an expert is responsible for analyzing the objects and properties of samples in thin sections under the microscope. The expert changes and fine-tunes the configurations of the microscope and camera until images that best represent the sample properties and elements are achieved. These past years witnessed the rise of fast and automated robotic microscopes that has motorized parts and cameras with pre-defined settings of capturing images. Images captured in these automated microscopes represent one or few setting configurations of many possibilities including orientation of microscope stage, magnification, focus or stage position, brightness, plane polarized light (PPL) versus cross polarized light (XPL) of the microscope, and brightness of the camera. Several previous works have proposed the capture of different images of one thin section with few different configurations to solve this problem. For example, to capture images that show different characteristics with different orientations one would take an image of the thin section at 0 degrees, 90 degrees, 180 degrees, and 360 degrees. The problem of the other option which is capturing a video or hundreds of images of one thin section showing the whole array of configurations is the massive output dataset. On the other hand, the problem of only capturing few configurations is that not all features and objects are distinguished and apparent in them to be detected by the automatic analysis programs.

To solve the problems associated with prior art systems, pre-defined ranges for the different settings are set by the user (1, 20×, 1, 1, 1, PPL). Also, the user has the option of choosing a course of action for changing the parameters such as magnification, focus, brightness, orientation, and selecting plane polarized light (PPL) versus cross polarized light (XPL). Next, the camera takes a picture and sends it to the computer system. The system utilizes different object detection programs to detect objects and properties of the image. As the computer system runs the analysis, it sends signals to the camera and microscope motorized parts to automate the change of the settings to a different configuration; it changes one parameter until all possible configurations for every parameter are covered. In the end, several pieces of information are saved. One, the images with the best analysis output reached by the detection programs and analyses close to the best are saved. Second pieces of information saved are the images regarded as "best". Third, the ranges of setting configurations that produced the best results are saved. These ranges represent logical ranges and would eliminate unnecessary configurations, thus reducing processing time for later thin sections.

In one embodiment, the system automatically picks several setting configurations of the camera and the microscope that result in the best image analysis. This analysis is deemed "best" as defined by different criteria. For example, one or more thin sections with their analysis already done could be used as training step where the images that produced analysis close to them are chosen as the "best". An image or "images" can be defined as "best" for analysis if it allows the detection and identification of most objects and properties in the whole area of thin sections. This means that all the setting configurations and the images resulted from them fall under two categories: the category with the best images and setting configurations defined previously, and the disregarded category of no analysis or minimal detection and identification caused by blurry images or too dark or too bright or out of focus images. Nevertheless, other scenarios might also occur. There could be images that result in a satisfactory analysis of some areas or zones of the thin section while other areas have no to minimal analysis. Moreover, the same areas of the thin section could have satisfactory but different analysis outputs. This means that one image of the same area was detected as a specific property or object (like porosity) while in the other image of the same area it was detected as a different property or object (like mineral). For that additional steps have to be impeded into the workflow of the expert system that automated this process.

First, the detection and analysis programs should have a workflow of detecting objects with properties that change with different setting configurations (for example, some mineral show different colors with different settings or stage orientations). This would not only solve the variability of the analysis output but it would also help in identifying these objects by the change of their properties. For that, the areas of the thin section have to be registered and referenced so they would be traced with changing settings.

Second, images that have areas which can only be analyzed by different configurations can be registered and stitched together. If area 1 of the thin section can be analyzed in image 1 while area 2 can only be analyzed in image 4, then the part of image 4 at area 2 should be cut and stitched over area 2 in image 1.

Third, an uncertainty calculation is run on the different analyses. The uncertainty is ranked based on the variability of detected objects and parameters of different configurations at the same zones of the thin section. Analyses of thin sections with variable but satisfactory outputs are ranked as high uncertainty and they are flagged for expert attention, while thin sections with repeated and similar analysis output are ranked low uncertainty.

Categorically, there are two problems with thin section images. First, thin sections images under the microscope are chosen by an expert or pre-defined settings, which means that these images represent the optimal settings configuration that the human eye could analyze the objects and features in such images and not what the automated programs can analyze since they are not involved in choosing the images. Second, thin section images represent one or few configurations of camera and microscope settings (orientation of microscope stage, magnification, focus, stage position, brightness, contrast, plane polarized light (PPL) versus cross polarized light (XPL)) which does not represent the full spectrum of possibilities. This limits the analysis of objects and features to one or few rather than all configurations.

Prior art methodologies either do not offer the methodologies or techniques this specification lists or they do not utilize the feedback of automated image analysis programs for quality check and for image configuration but rather they use pre-defined configurations that might not allow the analysis programs to pick all the features and objects that can potentially picked if this specification was applied.

Prior art methodologies also do not include the different procedures and methodologies enlisted in this specification including the quality check of the thickness consistency of samples, picking the best image capturing configuration. Also, even if different papers or patents propose the change of configurations during image capturing of thin section images they do not use the feedback from the automated image analysis programs as a way of quality check or for picking the best camera and microscope configurations but rather these different configurations are already set prior to the capture of images.

In one embodiment, the auto analyzer tool is a computer software that helps in configuring the settings of the camera and the microscope based on the output of the analysis program without the intervention of experts and to produce consistent and optimized analysis results.

The auto analyzer tool is connected to both the camera and microscope, and to the analysis program. This tool changes the settings on the camera and the microscope automatically after receiving certain outputs from the analysis program. These outputs are one of two types: Type one is 1 or 0 outputs. When the analysis program runs different operations like pattern recognition, and supervised expert system, to identify different features and objects it will produce a matrix grid where for every pixel the program has an answer or identification which would be given the number 1. However, because these analysis programs were built on best case scenario that might not be captured by every camera or microscope many pixels in these images would not be identifiable and given the number 0 for non-identifiable or noise. For that, the proposed specification tool allows the re-configuration of the camera or microscope until the image (termed "best") that has the most identifiable pixels is acquired.

Type two is the uncertain analysis output. Where the output answer for every pixel is either 0, 1, or 2. This means that under different settings the same pixel might have two or more different identification or analysis results. For that neural network is used to pick the settings with most consistent result that matches training images analyzed by an expert. The basic forward feed neural network would compare the analysis output of the image to the trading images and pick the settings that best match the trading set. This neural network could be replaced with a simple supervised and automated rules. In this case, the user has the choice when setting the auto analyzer of either accepting the analysis with most repetition or accepting all analyses.

For example there is a sample of red and blue colors wanted for automatic analysis, the analysis program interpret pixels with RGB values of (>50, 0, 0) as red, while pixels with RGB values of (0, 0, >50) with blue. The output analysis would be a grid with each pixel labels blue or red. However because the computer only "sees" images as numbers and because different configurations of the camera and the microscope would affect the captured image and consequently the information values of each pixel, some pixels might have no identification. In this example, all the pixels are either blue or red but because of the settings they were captured under they do not follow the criteria the analysis program was programmed to detect and interpret as such; blue color might lower or higher values if the brightness of the camera was too low or too high. On the other hand, sometimes red pixels would be interpreted as blue or vice versa under different setting configurations. For that the final "best" result would be either the analysis with the highest consistency (out of 1000 iterations 900 analysis reports identified pixel 1 as red), or the result would list the different analyses instead of one. The other option would allow the uncertainty measurement. Finally, there are cases where images would have the same number of identified number of pixels but not the same pixels identified. For example, pixel 1 would have an analysis and pixel 2 would not be identified in configuration 1 while pixel 1 has no analysis and pixel 2 has analysis in configuration 2. For that, the auto analyzer would enable the stitching of pixels from different images. This means that final "best" image would be constructed from pixels from images that have different setting configurations. A pixel with an analysis would replace the same pixel location where in an image where that pixel had no analysis or was not identified.

In one embodiment, the auto analyzer tool is not only meant to automate the change of the camera or microscope settings but also to pick the "best" images and settings. The user involvement or training has two aspects to it. One aspect is by choosing what sequence of camera or microscope parameters to change and also pre-define certain ranges of these parameters to avoid redundancy. Second aspect is a replacement to the mechanism of choosing "the best configurations or images" outlined previously. In this step, the user judges what images or configurations produce the best analysis and which do not. Based on these "answers" they system would build a one-layer neural network of what ranges and what sequence of parameter changing got the desired answers and apply them on the rest of images.

To understand the rule of the neural network in this specification, one must understand the input and outputs of the specification system. The system randomly chooses the configuration settings for the camera and microscope defined as numerical values spanning their defined ranges (for example, camera brightness=0-100%). An image is taken and sent to the analysis program. The analysis program returns a grid map of the image where, in addition to its vertical and horizontal coordinates, every grid pixel has either 0 or 1 values (for pixels with no analysis and pixels with analysis), or 0 or 1 or 2 or 3 . . . (0 is for no analysis and the numbers from 1 to . . . are numerical classes for different analysis identifiers ("Sand", "Clay", "Porosity"). The user has the choices of how the system selects the "best" images or configuration settings between 1) pre-defined automated rules set by the user or 2) neural network model that performs the job of the predefined rules. The predefined rules are basically simple programmed rules of if-statements and conditions (for example, if number of analyzed pixels in image>80%=>"best", if not=>"disregard"). The other option the user has the choice to select is training single layer neural network with already analyzed sample images.

For the choice of neural network, the user picks a couple of samples. Then the user supervises the analysis process by the analysis program and chooses the best analysis with the user's subjective judgment. The analysis results (X and Y coordinates of pixels, analysis identifier or class for every pixel) are used as a training data set or input. Then the system of camera or microscope is trialed with random configuration settings. The captured images are sent to the analysis programs producing all the analysis results possible. The new analysis results are correlated to the analysis results of the training set, creating a single layer neural network. This network is used to correlate which configuration settings are optimal to produce satisfactory analysis results of images. If the other samples come from the same field and prepared under the same conditions, their images would be captured using the configuration settings predicted by the neural network model.

The embodiments disclosed are configured to work with any image analysis program that may be suitable for the purpose including those based on image features using any type or any level of image processing. Additionally, the output of these image processing programs may include a grid map, based on for example the input image, with an identification classifier for every pixel or cell of the image. These identification classifiers may represent the analysis result and output of the image features analyzed by the disclosed program.

Figure 8:
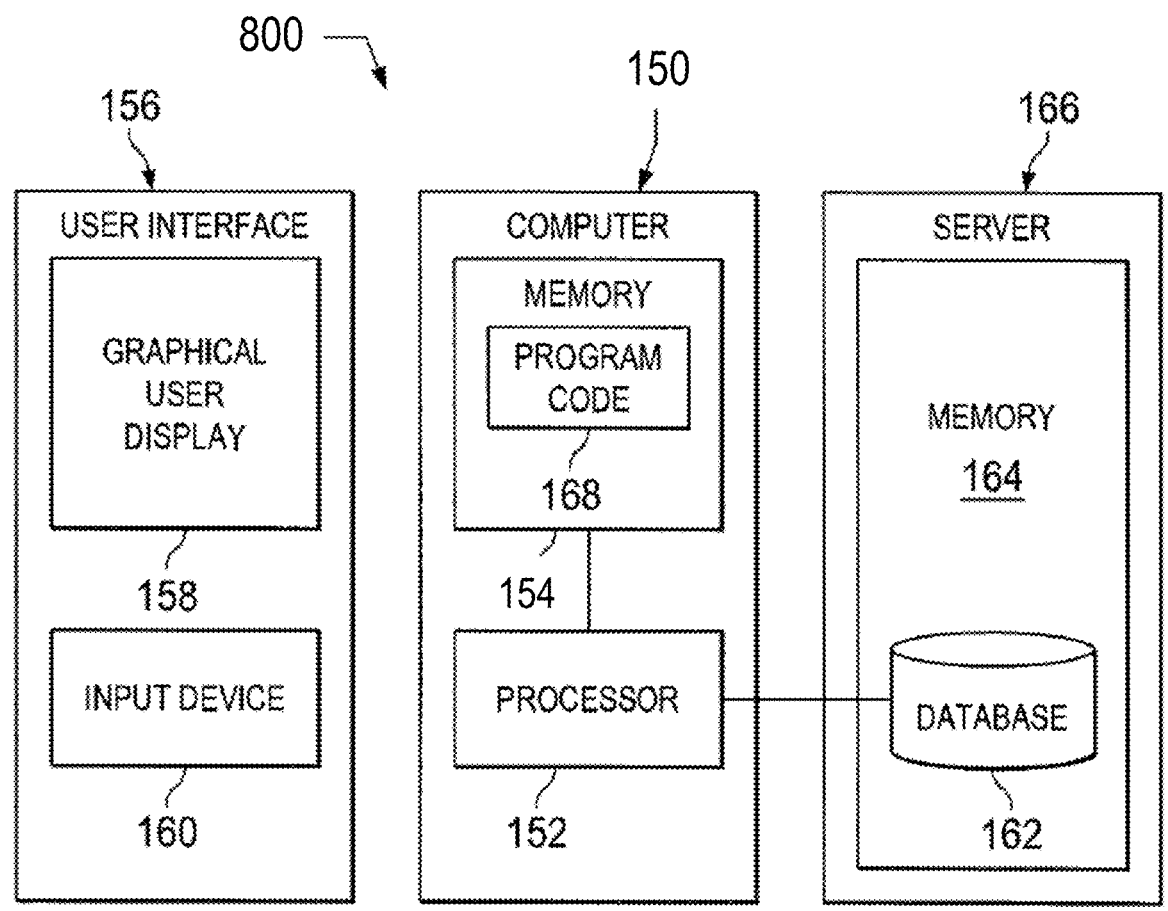
FIG. 8 illustrates a computer system for optimizing settings for a camera and microscope in accordance with an embodiment of the disclosure.

FIG. 8 illustrates a data processing system 800 for optimizing settings for a camera and microscope in accordance with an embodiment of the disclosure. As illustrated in FIG. 8, system 800 includes a computer 150 having a processor 152 and memory 154 coupled to processor 152 to store operating instructions, control information and database records. The computer 150 may be a portable digital processor, such as a personal computer in the form of a laptop computer, notebook computer or other suitable programmed or programmable digital data processing apparatus, such as a desktop computer. It should also be understood that the computer 150 may be a multicore processor with nodes such as those from Intel Corporation or Advanced Micro Devices (AMD), a High Performance Computing (HPC) Linux cluster computer or a mainframe computer of any conventional type of suitable processing capacity such as those available from International Business Machines (IBM) or other source.

The system 800 has a user interface 156 and an output data or graphical user display 158 for displaying output data or records of lithological facies and reservoir attributes according to this embodiment. The output display 158 includes components such as a printer and an output display screen capable of providing printed output information or visible displays in the form of graphs, data sheets, graphical images, data plots and the like as output records or images.

The user interface 156 of system 800 also includes a suitable user input device or input or output control unit 160 to provide a user access to control or access information and database records and operate the computer 150. Data processing system 800 further includes a database 162 stored in the computer memory, which may be internal memory 154, or an external, networked, or non-networked memory 164 in an associated database server 166.

The data processing system 800 includes program code 168 stored in memory 154 of the computer 150. The program code 168, according to this embodiment is in the form of non-transitory computer operable instructions causing the data processor 152 to perform the computer implemented method of the present disclosure in the manner described above.

It should be noted that program code 168 may be in the form of microcode, programs, routines, or symbolic computer operable languages that provide a specific set of ordered operations that control the functioning of the data processing system 800 and direct its operation. The instructions of program code 168 may be stored in non-transitory form in memory 154 of the computer 150, or on computer diskette, magnetic tape, conventional hard disk drive, electronic read-only memory, optical storage device, or other appropriate data storage device having a non-transitory computer usable medium stored thereon. Program code 168 may also be contained in non-transitory form on a data storage device such as server 166 as a computer readable medium.

The method of the present embodiment performed in the computer 150 can be implemented utilizing the computer program steps of FIGS. 3-7 stored in memory 154 and executable by system processor 152 of computer 150. The input data to processing system 800 are the input parameters and reservoir data of the types described above.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, that is, one or more modules of computer program instructions encoded on a tangible non-transitory storage medium for execution by, or to control the operation of, data processing apparatus. The computer storage medium can be a machine readable storage device, a machine-readable storage substrate, a random or serial access memory device, or a combination of one or more of them. Alternatively or in addition, the program instructions can be encoded on an artificially-generated propagated signal, for example, a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, for example, an FPGA (field programmable gate array) or an ASIC (application-specific integrated circuit). The apparatus can optionally include, in addition to hardware, code that creates an execution environment for computer programs, for example, code that constitutes processor firmware, a protocol stack, a database management system, an operating system, or a combination of one or more of them. A computer program, which may also be referred to or described as a program, software, a software application, an app, a module, a software module, a script, or code, can be written in any form of programming language (for example, compiled or interpreted languages, or declarative or procedural languages). A computer program can be deployed in any form, including as a stand-alone program or as a module, component, subroutine, or other unit suitable for use in a computing environment. A program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, for example, an FPGA or an ASIC, or by a combination of special purpose logic circuitry and one or more programmed computers. Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include (or be operatively coupled to share data with) one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device, for example, a universal serial bus (USB) flash drive, to name just a few. Computer-readable media suitable for storing computer program instructions and data include all forms of non-volatile memory, media and memory devices, including by way of example semiconductor memory devices, for example, EPROM, EEPROM, and flash memory devices; magnetic disks, for example, internal hard disks or removable disks; magneto-optical disks; and CD-ROM and DVD-ROM disks.

To provide for interaction with a user, embodiments of the subject matter described in this specification can be implemented on a computer having a display device, for example, a CRT (cathode ray tube) or LCD (liquid crystal display) monitor, for displaying information to the user and a keyboard and a pointing device, for example, a mouse or a trackball, by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, for example, a smartphone that is running a messaging application, and receiving responsive messages from the user in return.

Data processing apparatus for implementing machine learning models can also include, for example, special-purpose hardware accelerator units for processing common and compute intensive parts of machine learning training or production (for example, inference) workloads. Machine learning models can be implemented and deployed using a machine learning framework, for example, a TensorFlow framework, a Microsoft Cognitive Toolkit framework, an Apache Singa framework, or an Apache MXN framework.

Embodiments of the subject matter described in this specification can be implemented in a computing system that includes a back-end component, for example, as a data server, or that includes a middleware component, for example, an application server, or that includes a front-end component, for example, a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, for example, a communication network. Examples of communication networks include a local area network (LAN) and a wide area network (WAN), for example, the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, for example, a hypertext markup language ("HTML") page, to a user device, for example, for purposes of displaying data to and receiving user input from a user interacting with the device, which acts as a client. Data generated at the user device, for example, a result of the user interaction, can be received at the server from the device.

While this specification contains many specific implementation details, these should not be construed as limitations on the scope of the description in the specification or on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described earlier as acting in certain combinations and even initially be claimed as such, one or more features from a claimed combination can in some cases be excised from the combination, and the claimed combination may be directed to a sub combination or variation of a sub combination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described earlier should not be understood as requiring such separation in all embodiments, and it should be understood that the described program components and systems can generally be integrated together in a single software product or packaged into multiple software products.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used in the disclosure are for organizational purposes only and are not meant to be used to limit the scope of the description.

What is claimed is:

1. A method for optimizing settings for a camera and microscope for capturing thin section images of a reservoir rock in a hydrocarbon reservoir, the method comprising:
   (i) extracting a plurality of core samples from a well;
   (ii) cutting a respective plurality of thin sections from the plurality of core samples;
   (iii) capturing a thin section image using a robotic microscope and a camera;
   (iv) performing a frequency analysis of each pixel of the thin section image;
   (v) associating each pixel in the thin section image with a class identifier selected from a plurality of class identifiers, each class identifier associated with a range of frequencies;
   (vi) determining a percentage of pixels in each class identifier;
   (vii) determining a percentage of pixels comprising noise;
   (viii) saving the thin section image and the settings for the camera and microscope associated with the thin section image;
   (ix) saving data generated from the frequency analysis of the thin section image; and
   (x) saving the determination of the percentage of pixels comprising noise associated with the thin section image.

2. The method according to claim 1, further comprising:
   (xi) repeating steps (iv)-(x) for a plurality of thin section images taken at a plurality of settings for the camera and the microscope.

3. The method according to claim 2, further comprising:
   (xii) combining the settings for the camera and microscope associated with the plurality of thin section images, data generated from the frequency analysis of the plurality of thin section images, and the determination of the percentage of pixels comprising noise associated with the plurality of thin section images to produce a structured data set;
   (xiii) generating a machine learning model using the structured data set; and
   (xiv) determining, using the machine learning model, an optimized setting for the camera and an optimized setting for the microscope based on the thin section image with the least noise.

4. The method according to claim 3, wherein the optimized setting comprises at least one setting for orientation of microscope stage, magnification, brightness, contrast, illumination, stage position, plane polarized light (PPL), cross polarized light (XPL), thin focus, and coarse focus.

5. The method according to claim 2, wherein the plurality of settings comprise orientation of microscope stage, magnification, brightness, contrast, illumination, stage position, plane polarized light (PPL), cross polarized light (XPL), thin focus, or coarse focus.

6. The method according to claim 1, wherein the step of determining a percentage of pixels comprising noise further comprises determining a percentage of pixels having a frequency over a predetermined threshold.

7. The method according to claim 1, wherein the machine learning model comprises an artificial neural network (ANN), a support vector machine (SVM), a radial basis function (RBF), fuzzy logic, a decision tree, random forest, or k-means algorithm.

8. A system comprising:
   a microscope configured to take images of a plurality of petrographic thin section samples and create petrographic thin section sample digital image files from the images, and
   a computer system comprising a processor and a non-transitory computer readable storage medium in data communication with the processor storing instructions executable by the processor and that upon such execution causes the processor to perform operations comprising:
   (i) performing a frequency analysis of each pixel of the thin section image;

(ii) associating each pixel in the thin section image with a class identifier selected from a plurality of class identifiers, each class identifier associated with a range of frequencies;
(iii) determining a percentage of pixels in each class identifier;
(iv) determining a percentage of pixels comprising noise;
(v) saving the thin section image and the settings for the camera and microscope associated with the thin section image;
(vi) saving data generated from the frequency analysis of the thin section image; and
(vii) saving the determination of the percentage of pixels comprising noise associated with the thin section image.

9. The system according to claim 8, further comprising the operations of:
(viii) repeating steps (i)-(vii) for a plurality of thin section images taken at a plurality of settings for the camera and the microscope.

10. The system according to claim 9, further comprising the operations of:
(ix) combining the settings for the camera and microscope associated with the plurality of thin section images, data generated from the frequency analysis of the plurality of thin section images, and the determination of the percentage of pixels comprising noise associated with the plurality of thin section images to produce a structured data set;
(x) generating a machine learning model using the structured data set; and
(xi) determining, using the machine learning model, an optimized setting for the camera and an optimized setting for the microscope based on the thin section image with the least noise.

11. The system according to claim 10, wherein the optimized setting comprises at least one setting for orientation of microscope stage, magnification, brightness, contrast, illumination, stage position, plane polarized light (PPL), cross polarized light (XPL), thin focus, and coarse focus.

12. The system according to claim 9, wherein the plurality of settings comprise orientation of microscope stage, magnification, brightness, contrast, illumination, stage position, plane polarized light (PPL), cross polarized light (XPL), thin focus, or coarse focus.

13. The system according to claim 8, wherein the step of determining a percentage of pixels comprising noise further comprises determining a percentage of pixels having a frequency over a predetermined threshold.

14. The system according to claim 8, wherein the machine learning model comprises an artificial neural network (ANN), a support vector machine (SVM), a radial basis function (RBF), fuzzy logic, a decision tree, random forest, or k-means algorithm.

15. A non-transitory computer readable storage medium storing instructions executable by a data processing apparatus and that upon such execution causes the data processing apparatus to perform operations comprising:
(i) receiving a thin section image;
(ii) performing a frequency analysis of each pixel of the thin section image;
(iii) associating each pixel in the thin section image with a class identifier selected from a plurality of class identifiers, each class identifier associated with a range of frequencies;
(iv) determining a percentage of pixels in each class identifier;
(v) determining a percentage of pixels comprising noise;
(vi) saving the thin section image and the settings for the camera and microscope associated with the thin section image;
(vii) saving data generated from the frequency analysis of the thin section image; and
(viii) saving the determination of the percentage of pixels comprising noise associated with the thin section image.

16. The medium according to claim 15, further comprising the operations of:
(ix) repeating steps (ii)-(viii) for a plurality of thin section images taken at a plurality of settings for the camera and the microscope.

17. The medium according to claim 16, further comprising the operations of:
(x) combining the settings for the camera and microscope associated with the plurality of thin section images, data generated from the frequency analysis of the plurality of thin section images, and the determination of the percentage of pixels comprising noise associated with the plurality of thin section images to produce a structured data set;
(xi) generating a machine learning model using the structured data set; and
(xii) determining, using the machine learning model, an optimized setting for the camera and an optimized setting for the microscope based on the thin section image with the least noise.

18. The medium according to claim 16, wherein the plurality of settings comprise orientation of microscope stage, magnification, brightness, contrast, illumination, stage position, plane polarized light (PPL), cross polarized light (XPL), thin focus, or coarse focus.

19. The medium according to claim 15, wherein the step of determining a percentage of pixels comprising noise further comprises determining a percentage of pixels having a frequency over a predetermined threshold.

20. The medium according to claim 15, wherein the machine learning model comprises an artificial neural network (ANN), a support vector machine (SVM), a radial basis function (RBF), fuzzy logic, a decision tree, random forest, or k-means algorithm.

* * * * *